US00PP27897P3

(12) United States Plant Patent
Nixon et al.

(10) Patent No.: US PP27,897 P3
(45) Date of Patent: Apr. 18, 2017

(54) APRICOT TREE NAMED 'NZSUMMER3'

(50) Latin Name: *Prunus armeniaca*
Varietal Denomination: Nzsummer3

(71) Applicant: The New Zealand Institute for Plant and Food Research, Auckland (NZ)

(72) Inventors: Arlene E. Nixon, Alexandra (NZ); Michael T. Malone, Havelock North (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 105 days.

(21) Appl. No.: 14/544,858

(22) Filed: Feb. 26, 2015

(65) Prior Publication Data

US 2015/0250081 P1 Sep. 3, 2015

Related U.S. Application Data

(60) Provisional application No. 61/946,596, filed on Feb. 28, 2014.

(51) Int. Cl.
*A01H 5/08* (2006.01)

(52) U.S. Cl.
USPC ..... Plt./186

(58) Field of Classification Search
USPC ..... Plt./186
See application file for complete search history.

*Primary Examiner* — Keith Robinson
(74) *Attorney, Agent, or Firm* — Lathrop & Gage LLP

(57) ABSTRACT

A new and distinct apricot variety is described. The variety results from selection among a population of seedlings derived from controlled crossing of the varieties 'Bhart' (not patented), marketed as Orangered™ and 'Late Moorpark' (not patented). The new variety, initially designated StB14/15 and now designated Nzsummer3, is distinguished from others by medium sized fruit with a deep red overcolour when mature accompanied by mid orange coloured firm flesh and low ethylene characteristics. Fruit of Nzsummer3 matures in early to late February in Otago, New Zealand.

4 Drawing Sheets

Genus and species of plant claimed: *Prunus armeniaca.* Variety denomination: 'Nzsummer3'.

BACKGROUND OF THE INVENTION

Seedlings obtained from the deliberate crossing of the apricot varieties 'Bhart' (not patented) (female parent), and 'Late Moorpark' (not patented) (male parent), in September 2001, were planted out at the Clyde Research Station of The New Zealand Institute for Plant and Food Research Limited, where the cross was also conducted. In February 2006, Nzsummer3 (originally designated as StB14/15) was identified to have potential as a new variety. Later in 2006, Nzsummer3 was asexually propagated by budding onto 'Golden Queen' (not patented) peach seedlings, the standard apricot rootstock in New Zealand. The resulting trees were planted out on the Clyde Research Station in the Southern Hemisphere winter of 2007, and were subsequently found to be true to type demonstrating that the characteristics of the new variety, Nzsummer3, are stable and transmitted without change through succeeding generations.

SUMMARY OF THE INVENTION

Nzsummer3 is characterised by medium sized fruit (70-90 g) with a deep red overcolour, mid orange colour firm flesh and low ethylene characteristics which mature in early-late February in Otago, New Zealand. Nzsummer3 is distinguished from a number of other varieties by the following characteristics:

Nzsummer3 has firmer flesh and a longer harvest window when compared to 'F168' (U.S. Plant Pat. No. 16,071) (also known as 'Larclyd', marketed as Genevieve) grown under the same conditions.

Nzsummer3 has smaller fruit on average than 'F194' (U.S. Plant Pat. No. 16,119), Nzsummer3 fruit is approximately 70-90 g while 'F194' is approximately 100 g.

Nzsummer3 can be distinguished from its parent 'Late Moorpark' as 'Late Moorpark' at harvest maturity has higher soluble solid content, on average 22% while Nzsummer3 is 17%. 'Late Moorpark' fruit have a tendency to crack at harvest maturity while Nzsummer3 does not show this tendency.

Nzsummer3 can be distinguished from its parent 'Bhart' as the harvest season of 'Bhart' is early while Nzsummer3 is late. 'Bhart' harvests approximately one month earlier than Nzsummer3.

BRIEF DESCRIPTION OF PHOTOGRAPHS

The accompanying photographs show typical specimens of the plant, fruit, and leaves of the new variety was depicted in colours as nearly true as is reasonably possible to make the same colour in illustrations of this character.

Figure 1:
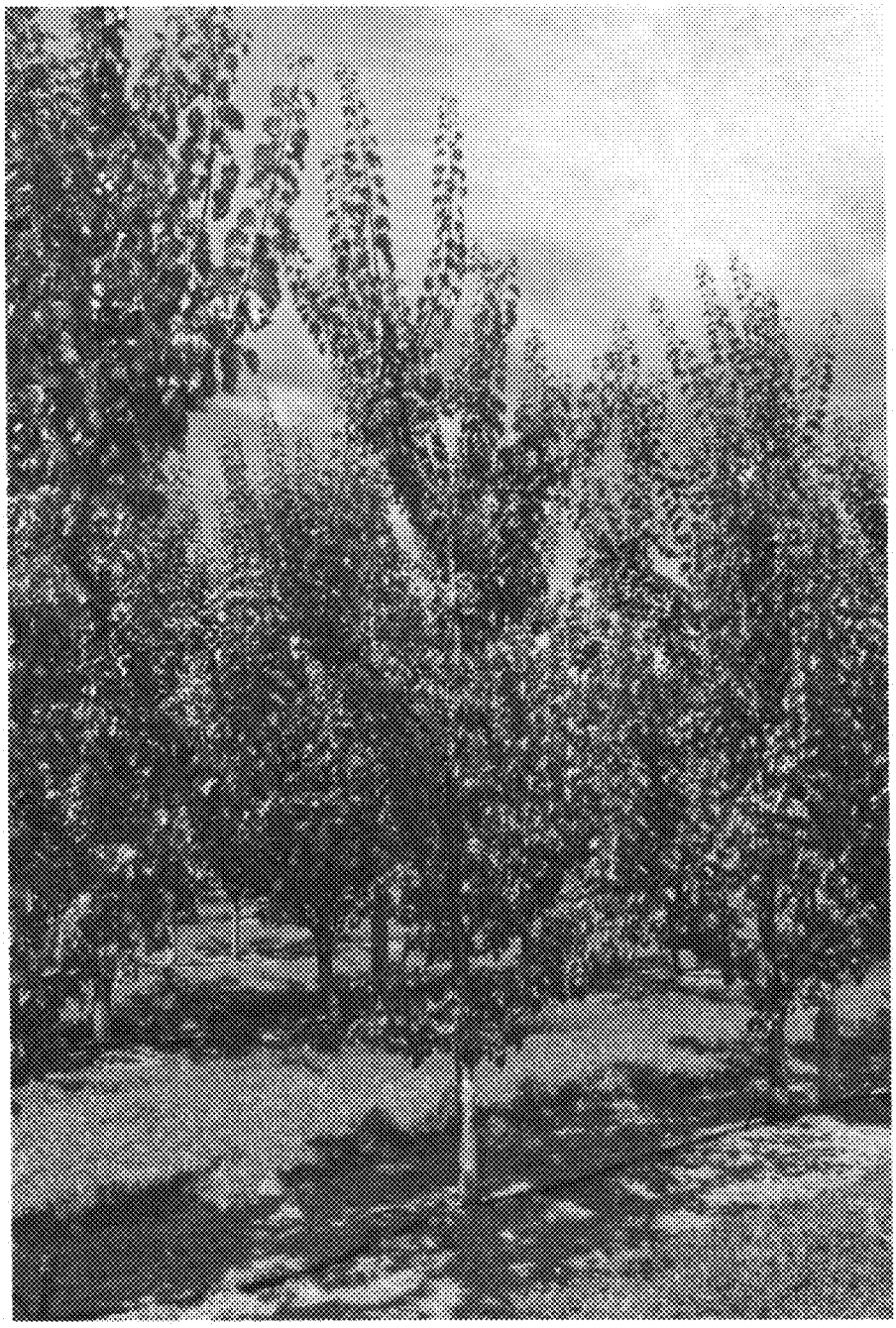
Figure 2:
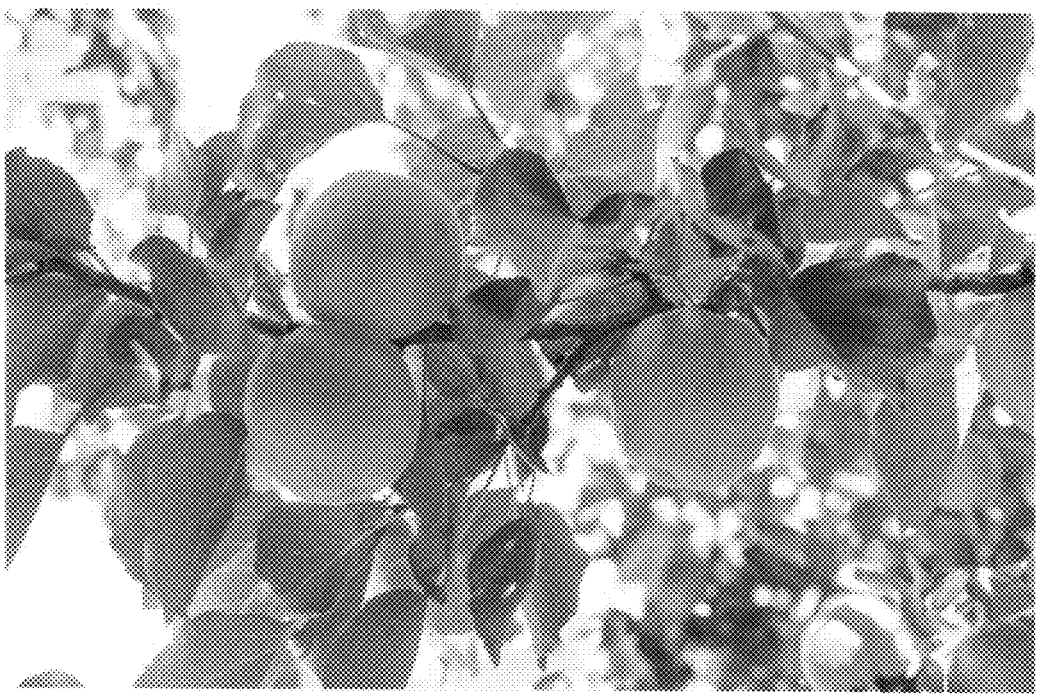
Figure 3:
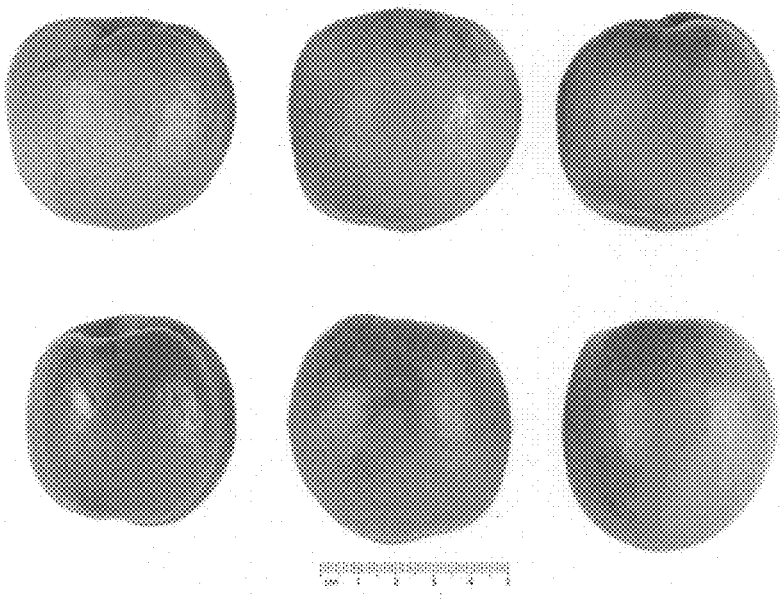
Figure 4:
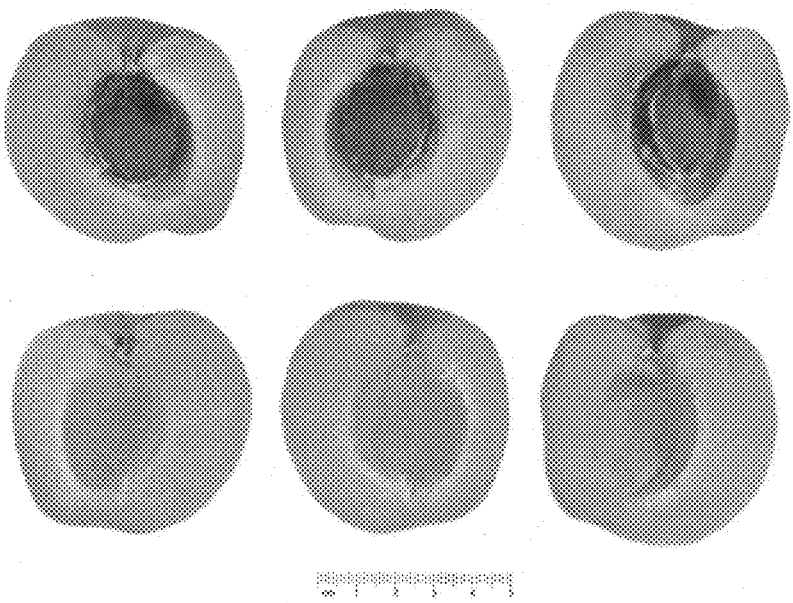
Figure 5A:
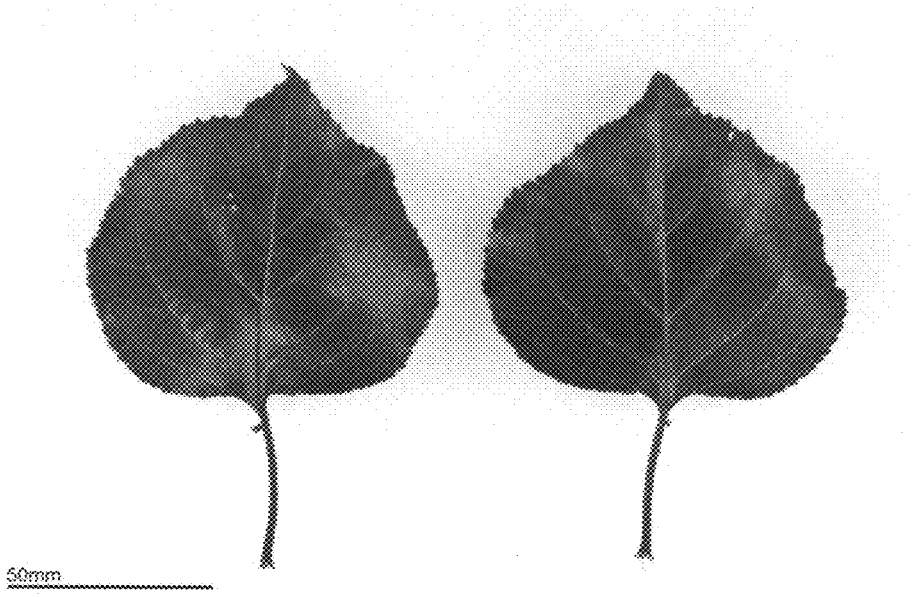
Figure 5B:
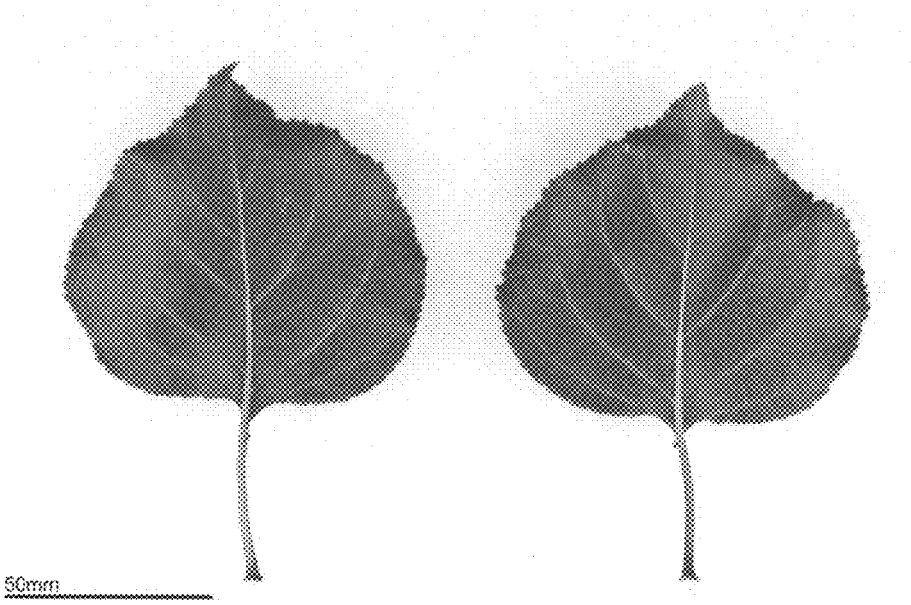

FIG. 1: Six year old Nzsummer3 tree, in summer.
FIG. 2: Nzsummer3 fruit on the tree.
FIG. 3: Nzsummer3 whole fruit.
FIG. 4: Longitudinal section of Nzsummer3 fruit.
FIGS. 5A and 5B: Upper (5A) and underside (5B) of Nzsummer3 leaves.

DETAILED DESCRIPTION

The following is a description of the new variety with colour terminology in accordance with The Royal Horticultural Society Colour Charts (R.H.S.C.C.) Fifth edition (2007). The specimens described were grown in Clyde, New Zealand. The observations were made of the 2013-2015 seasons on 5-7 year old mature trees.

Tree: Tree habit is upright to spreading with medium vigour. Nzsummer3 scions are compatible on peach seedlings ('Golden Queen') rootstocks. Tree health is considered to be good under Central Otago conditions in New Zealand with a medium level of precocity compared to commercially grown varieties under similar conditions.

Trunk: The average circumference of a mature trunk, approximately 30 cm from the graft union was 45 cm. The trunk colour was observed to be near brown N200, with a medium rough bark texture, and a medium density distribution of near greyed white 159B lenticular shaped lenticels which averaged approximately 3 mm long×1.2 mm wide.

Leaves: The leaves examined were fully expanded and harvested from the central third of growing shoots in summer. The overall shape of the leaf was observed to be ovate with a broad long acuminate tip approximately 14 mm long, a truncate base and serrate margins with medium undulation. Leaves are arranged alternatively and averaged 85 mm long and 78 mm wide and the profile in cross section was moderately concave. The colour of the upperside was near green 137B with a matt gloss, the colour of the underside was near 147B and the colour of the venation was near yellow green 146D.

Petiole: Examined in summer, the average length of fully expanded leaves was 45 mm and 3 mm in diameter. The upperside of the petioles had anthocyanin colouration of near greyed purple 187B and the underside was near greyed purple 184A. Petioles were observed to have between two and three nectaries close to the leaf base which had an average diameter of 1.2 mm.

Flowers: Flower buds were equally distributed on spurs and on one year old shoots. Full bloom, 90% of flowers open, was recorded as occurring in early September (approximately 7 September). The average diameter of the flower was 30 mm. The petal shape was circular and had an average length of 13 mm and average width of 11 mm. The petal colour was near red purple, 69D.

Fruit: Fruit at horticultural maturity were medium sized and observed to have an average fruit weight of between 70-90 g with an average height of 55.5 mm, average lateral width of 54.9 mm, and average ventral width of 49.7 mm. Nzsummer3 fruit were slightly asymmetric and were circular in lateral view and elliptic in ventral view with a slightly sunken suture and a truncate apex. The stalk cavity was medium in depth, approximately 3.2 mm deep. The skin surface was smooth with minimal pubescence, had weak gloss, and a background colour of near orange 25B with a medium, approximately 25-40% relative area of overcolour. The overcolour was coloured near red 46A made up of a solid flush and isolated flecks. The flesh colour was near orange 25B and near orange 25B in the stone cavity with some whiteness around the stone. The flesh texture was fine and firm, with a weak adherence to the stone and average soluble solids of approximately 17%. The fruit had a mild, low acid flavor.

Stone: Observations were made on dry stones unless otherwise stated. Stones were ovate in lateral view and had a rounded apex and truncate base. Stones on average weighed approximately 4.2 g, and were approximately 27.2 mm long with an average lateral width of 22.7 mm. The stone was coloured near grey brown 199A.

Harvest timing: Fruit begin ripening late in the season, approximately 10-17 February in Clyde, New Zealand. Average fruit yield was 43 tonne/ha.

Use: Fresh eating.

Pest and disease: Nzsummer3 has no particular tolerances or susceptibilities to pests and diseases associated with apricot trees.

Keeping quality: Has been shown to store very well for at least four weeks at 0° C. Nzsummer3 is a low ethylene producer, the recorded ethylene production from mature fruit held at 20° C. for 10 days was recorded as approximately 0-0.0008 nmol/kg/s.

The invention claimed is:

1. A new apricot plant substantially as illustrated and described.

* * * * *